United States Patent [19]

Fränzl et al.

[11] Patent Number: 5,432,086
[45] Date of Patent: Jul. 11, 1995

[54] APPARATUS FOR THE AUTOMATIC MONITORING OF MICROORGANISM CULTURE

[75] Inventors: Gert Fränzl, Purkersdorf; Helmut Pfützner, Bad Gastein; Karl Futschik, Maria Enzersdorf, all of Austria

[73] Assignee: Sy-Lab Vertriebsgellschaft M.B.H., Purkersdorf, Austria

[21] Appl. No.: 168,820

[22] Filed: Dec. 16, 1993

[51] Int. Cl.⁶ ............................................. C12M 1/34
[52] U.S. Cl. .............................. 435/291; 422/82.02; 324/447; 324/692
[58] Field of Search .................. 435/29, 34, 39, 40, 435/287, 291, 296, 297, 298, 301, 817; 422/82.01, 82.02; 324/439, 444, 445, 446, 447, 450, 691, 692, 71.1; 364/496, 482, 483, 413.01; 374/166, 167

[56] References Cited

U.S. PATENT DOCUMENTS

| | | | |
|---|---|---|---|
| 3,331,247 | 7/1967 | Toepell | 374/167 |
| 3,890,201 | 6/1975 | Cady | 435/291 |
| 3,984,766 | 10/1976 | Thornton | 324/692 |
| 4,067,951 | 1/1978 | Fleming et al. | 264/272 |
| 4,160,205 | 7/1979 | Hobbs et al. | 324/65 R |
| 4,230,983 | 10/1980 | Steere et al. | 324/71.1 |
| 4,250,266 | 2/1981 | Wade | 435/291 |
| 4,914,378 | 4/1990 | Hayashi et al. | 324/696 |

FOREIGN PATENT DOCUMENTS 0233024 8/1987 European Pat. Off.
392798 6/1991 Germany.

Primary Examiner—William H. Beisner
Attorney, Agent, or Firm—Herbert Dubno

[57] ABSTRACT

Impedance measurements from an array of cells containing microorganisms whose growth or multiplication are to be measured in terms of the impedance, utilizes electrodes which can be introduced into the cells and have contact pieces engageable by one or more probes of a measuring head displaceable by an x, y carriage system into alignment with the successive contact pieces. The system avoids the need for voluminous conductor arrangements and multiplexing systems.

10 Claims, 2 Drawing Sheets

APPARATUS FOR THE AUTOMATIC MONITORING OF MICROORGANISM CULTURE

SPECIFICATION

1. Field of the Invention

Our present invention relates to an apparatus for monitoring microorganism growth or multiplication and, more particularly, to an apparatus for the fully-automatic determination of microorganism multiplication or cultivation in a multiplicity of cells by the measurement of an electrical impedance in each cell with a plurality of electrodes.

2. Background of the Invention

To determine the bacterial count of microorganism cultures, increasingly fully-automatic computer-controlled processes are employed which can use, inter alia, a measurement of an electrical impedance to indicate the bacterial count or the extent to which a culture has grown or the microorganisms in a culture have multiplied.

The liquid sample can be provided in a measurement cell into which two electrodes can be inserted or which can be provided with two electrodes to enable an electrical impedance between the electrodes to be measured (see for example EP-A-233,024). In modern apparatus, generally a multiplicity of cells may be provided and the impedance measured in each cell under the control of a computer. In such systems, the cells are cyclically monitored through a multiplexer at time intervals of several minutes by being connected to an impedance measuring device. The development of the culture is thereby indicated by a corresponding time rate of change of the measured impedance values.

The number of cells which can be utilized in such systems is, in principle, unlimited. However, with increasing numbers of cells a correspondingly large number of conductors must be provided and these must be associated with a corresponding number of multiplexer channels (see, for example, U.S. Pat. Nos. 3,890,201, 4,160,205 and 4,067,951).

Especially voluminous conductor systems arise with processes which not only detect the total impedance of each cell but break down the complex total impedance Z into the impedance $Z_M$ of the liquid medium and the impedance contribution $Z_E$ of the measurement electrodes (see AT-B 392 798). In this case, up to four electrodes are required, thereby increasing the complexity of the conductor systems and the multiplexer systems and increasing the possibility of failure as a result.

Processes in which contact arrangements are permanently mounted in each cell are also disadvantageous because of high fabrication cost and because totally disposable cell plates are desirable.

Large numbers of cells in a system have also created a number of other problems with respect to the monitoring of samples for specific purposes. For example, the impedance technique is largely nonspecific and thus is difficult to use for selective determination of microorganisms. It is, therefore, necessary to run multiple test series in specifically created culture media in order to make determinations which are selective with respect to particular microorganisms. This, of course, is also complicated by the need for large numbers of conductors and multiplexer channels in conventional measuring systems.

One method of avoiding voluminous conductor and contact systems is to successively connect the cells cyclically and individually to the measuring electrodes of an impedance measuring device. In U.S. Pat. No. 4,250,266, for example, a carousel arrangement of the measuring cells is provided and, with stepwise rotation of the carousel, the measuring cells are brought into engagement with spring contacts.

This arrangement has the drawback that the geometry, arrangement and number of cells is greatly limited and, for a given area is generally fixed. Because of the large number of microorganisms which generally must be monitored and the different requirements with respect to optimum cell size and the number of samples which can be provided in a particular area, these limitations are especially problematical. From the point of view of flexibility and versatility, it is desirable to utilize cells which are of inexpensive and simple construction, are disposable, and can be provided in varying numbers of varying size in or on respective cell plates.

With earlier systems which eliminate the multiplexer between probe and the impedance measuring circuit, frequently the problem of contact resistance arises because different cells do not have the same contact resistance with respect to the probe in conventional arrangements.

The contribution of a significant contact resistance R to the total impedance Z may often be as large as the changes in the total impedance which are measured to monitor the microorganism growth. Since in cycling with cycle times of several minutes, the change in total impedance Z can be greatly falsified by the contact resistance R or changes therein from cell to cell or measurement to measurement, the measurement results can be made unreliable.

OBJECTS OF THE INVENTION

It is, therefore, the principal object of the present invention to provide an apparatus which overcomes substantially all of the aforementioned drawbacks and can provide reliable and accurate monitoring of the microorganism growth or multiplication.

More specifically, it is an object of this invention to provide an apparatus which eliminates the need for voluminous and bulky conductor systems and multiplexer arrangements and which allows a more versatile geometry of the measurement cells while removing limitations as to cell size and number characterizing earlier microorganism culture measurement systems.

A further object of the present invention is to provide a highly effective apparatus for monitoring microorganism growth and multiplication by an impedance measuring process which is less sensitive to contact resistance than earlier systems.

It is also an object of the invention to provide, in an impedance measuring system of an improved type, a contact arrangement which will minimize the contribution of contact resistance R to measured values of the impedance Z or will permit correction for the contact resistance in a reproducible and reliable manner so that there will be no significant contribution of a contact resistance value to falsification of an impedance measurement result.

SUMMARY OF THE INVENTION

These objects and others which will become apparent hereinafter are attained, in accordance with the invention by providing the electrodes with electrode contacts or electrode contact pieces lying wholly outside the cells but electrically connected to the portions of the electrodes which extend into the samples in the cell, and a measurement head which is shiftable by a slide or rail system and electrically connects with these contacts or contact pieces to in turn selectively connect them to the impedance measuring circuit.

With the invention, of course, the cells are provided which are spaced from the electrode contacts or contact pieces and thus the contents of the cell cannot contribute contact resistance errors upon engagement of the head with the contact.

It has been found to be advantageous, moreover, to provide the contact or contact piece with a contact area which is substantially greater than the cross sectional area of the pin forming the electrode and to ensure a practically zero resistance electrical connection between the contact piece and the electrode pin. With large areas of contact between the sensing head and the contact piece, there is practically zero contact resistance anywhere in the path between the sample and the impedance measuring circuit.

The head is displaceable by the slide carriage and rail system and can be brought into contact with the contact pieces of the cells in succession so that the measured values of the impedance in the cells are determined one after the other so that complex wiring and multiplexers can be avoided. The arrays of cells can be columns and rows of spaced-apart cells so that the rail and carriage system can move the head parallel to the columns and rows in steps equal to the cell spacing.

It has been found to be advantageous to provide the electrodes on a common electrode carrier which can be raised from the upwardly open cells, themselves on a cell plate or formed in a cell plate.

In this case, the electrode contact pieces can be provided on the upper side of the electrode carrier, i.e. on a side opposite that from which the electrode pins project into the respective cells.

The cell array containing the samples of the microorganism culture can thus be disposed below the electrode carrier which can therefore have a cover function preventing contact with the contents of the cells by the personnel and contamination of the samples by ambient particles. The electrodes, preferably pin electrodes, have a spacing such that they dip into the samples in the respective cells and therefore project from the underside of the electrode carrier while the contact pieces of these pins are disposed in the same geometrical array as the cells on the upper surface of the carrier and thus are freely accessible to the measurement head.

These contact pieces can be formed simply as heads at the ends of the electrode pins opposite pointed tips thereof which engage in the samples.

The electrode carrier as a whole with the electrodes thereon can be subjected to a variety of chemical or physical cleaning processes or to treatments which allow the electrodes to be used with increased specificity to detect particular organisms. For reusable electrode systems, the carrier with the electrodes thereon can be autoclaved.

The arrangement of the electrode contact pieces and thus the sensing head above the cells also has the advantage that contamination of the electrode contact pieces and/or the head by the contents of the cells is precluded.

When the cell arrays are formed in a cell plate, for example, the cell plates can be disposable. The array of cells and hence of the electrode contact pieces, can be a two-dimensional array with rows or columns spaced apart along the x and y axes and the positioning of the head and the stepping of the head from electrode contact piece to electrode contact piece can be effected by computer control.

For exact alignment of the contacts of the contact plate with the head and hence precise contact of the probe of the head with the contact pieces, the contact head can be provided with a sensor for automatic detection of the electrode contact piece with which its probe is to be aligned. The sensor system may be optical, magnetic or electrical in nature and in the latter case, the contact system itself may be employed to determine the positioning of the head.

The head is cyclically positioned above the individual cells and the sensing probe or contacts can be lowered, for example, magnetically, to engage the juxtaposed electrode contact piece against which it is pressed or rubbed.

The cyclical positioning can be effected for two computer-controlled stepping motors of an x-y carriage system. To accelerate the sensing process, the head may be provided with probes enabling simultaneous engagement with the contact pieces of several cells and in a particularly simple case with the contact pieces of an entire row of cells.

While the sensing head can have in principle a plurality of probes each engageable with a contact piece of one of the electrodes of each cell, where two or more electrodes are provided for each cell, it has been found to be advantageous to provide one electrode of each cell as a ground electrode and to connect all of the ground electrodes together by a common ground conductor of the electrode carrying plate. In this simple case, the contact system includes one contact per cell connected to a single metal tip which forms the electrode projecting into the cell while the probe in turn is a single metal point engageable with the contact pieces from above in succession.

It has been found to be advantageous for the detection of contact errors and to effect appropriate correction to provide the sensing contact from a plurality of partial contacts. For this purpose two galvanically interconnected metal tips A and B can be provided. In a first step, the metal tip A is lowered to engage the electrode contact piece and a total impedance value $Z_1 = Z + R_A$ is measured, where $Z_1$ is the measured value of the impedance by the tip A and $R_A$ is the contact resistance between the contact piece of the electrode and this tip. In addition, contact piece B engages the contact to provide an impedance measurement $Z_2 = Z + (R_A R_B/(R_A + R_B))$ where $R_B$ is the contact resistance of the contact B. As the contact point A retracts, the impedance measurement $Z_3 = Z + R_B$ can be obtained.

From these three equations, it is possible to determine the three unknowns Z, $R_A$ and $R_B$ and, of course, this yields the value of principal interest, namely, the impedance Z. If it is desirable to obtain a breakdown of the total impedance Z into the impedance $Z_M$ of the liquid medium and each impedance $Z_E$ of the measurement electrodes, each cell can have up to four electrodes with respective contact pieces engaged by respective probes of the contact head.

More specifically, the apparatus for the fully automatic monitoring of microorganism multiplication can comprise:

a support provided with a multiplicity of cells containing respective samples of a microorganism culture;

at least one electrode assigned to each of the cells and adapted to contact the respective sample for an electrical measurement of an electrical impedance thereof;

respective contacts externally of the cells electrically connected to each of the electrodes and disposed in an array;

a sensing head successively juxtaposable with the contacts and provided with a probe engageable with the contacts with which the head is juxtaposed and connected to an impedance measuring circuit; and a traveling carriage system defining paths parallel to rows of the contacts along the array and displacing the head along the paths.

BRIEF DESCRIPTION OF THE DRAWING

The above and other objects, features and advantages of the invention will become more readily apparent from the following description, reference being made to the accompanying highly diagrammatic drawing in which.

SPECIFIC DESCRIPTION

Figure 1:
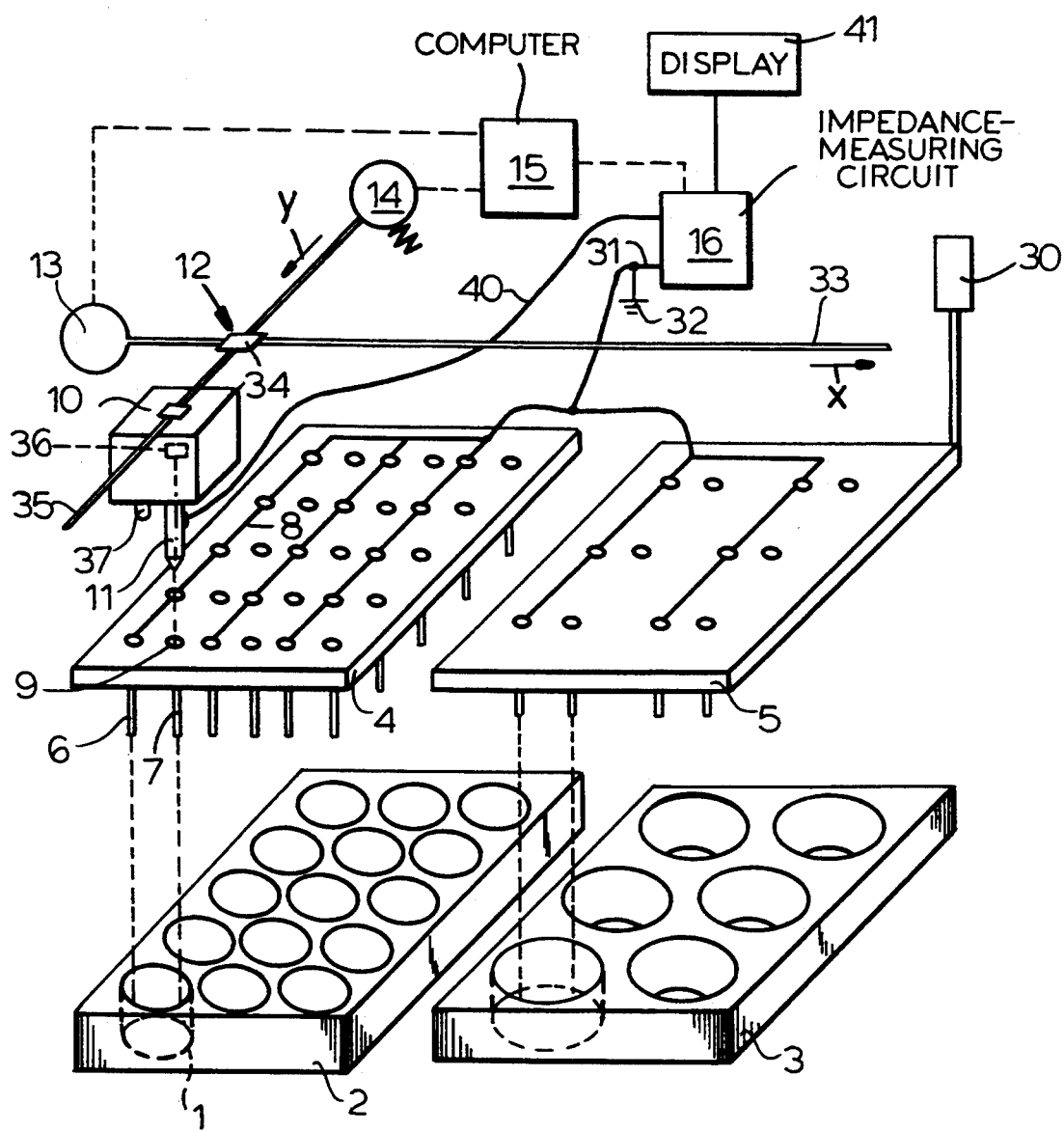
FIG. 1 is a simplified perspective view illustrating the principles of the invention in somewhat exploded form.

FIG. 1 shows two cell plates 2 and 3, each of which is provided with a rectangular array of measurement cells 1 in rows and columns and which can be filled with the culture medium containing the microorganisms which multiply in the respective culture medium. The plate 2 has fifteen such cells and the plate 3 has six cells, the latter cells being of larger diameter.

Each of the plates 2 and 3 is associated with an electrode carrier 4 and 5 here shown to be lifted out of engagement with the medium in the cells but normally disposed closer to the plates 2 and 3 so that two electrodes 6, 7 in the form of conductive pins penetrate into the medium in each cell. The means for raising and lowering the electrode plates 4 and 5, which are composed of nonconductive material, is represented at 30 in FIG. 1 and can be a linear electric motor, a pneumatic or hydraulic device, or simply a guide for the plates 4 and 5 which has a manually-operated spindle enabling them to be raised and lowered. In their lowered positions, of course, the plates 4 and 5 cover the plates 2 and 3.

Each of the cells 1 receives, in the simplest version of the apparatus illustrated, two electrodes of which one, the left-hand electrode 6, seen in FIG. 1, is a grounding electrode connected on the surface of the electrode plate 4 or 5 turned away form the cells 1, by a grounding conductor 8 which may be connected at 31 to the impedance-measuring circuit 16 and the ground as represented at 32.

The right-hand electrodes 7 of each electrode pair, 6, 7, have plate-like contact pieces 8 on the surface of the electrode carrier plates 4 and 5 turned away from the cells, these contacts 9 being spaced with the regularity and spacing of the cells.

Above the electrode carriers 4 and 5, a sensing head 10 is displaceable in the x and y directions by a coordinate sliding carriage arrangement represented generally at 12. This system can include a spindle 33 extending perpendicular to the columns but parallel to the rows and driven by a stepping motor 13. The spindle is provided with a carriage 34 displaceable in the x direction and bearing the spindle 35 and the stepping motor 14 which displaces the head 10 in the y direction, i.e. along the columns.

The head 10, shown in its most forward extreme lefthand position, is provided with a probe or head contact 11 which can be raised and lowered so that, in its lowered position, it engages the contact 9 of the respective electrode 7.

The means for raising and lowering the probe 11 is represented at 36 in the head 10. In addition, the head 10 can have a proximity sensor 37 for locating each contact 9 and positioning the head 10 so that its probe 11 is fully aligned with the contact 9.

The stepping motors 13 and 14 are operated by a computer 15 to successively step the head from contact piece 9 to contact piece 9, thereby allowing successive impedance measurements to be taken. The electrical connection between the probe 11 and the impedance-measuring circuit 16 is represented at 40 in FIG. 1.

In operation, once the cell plates 2 and 3 are positioned below the electrode-carrying plates 4 and 5 having the same array spacing of electrodes as the spacing of the respective cells of the sample plates therebelow and the computer 15 is programmed to align the head 10 with the contacts 9 of the plates 4 and 5, the plates 4 and 5 are lowered so that their electrodes 6 and 7 are immersed in the medium in each cell 1. The head 10 is then displaced by the x, y slide arrangement 12 with, for example, the head being stepped first along the contacts 9 of one column and then along the contacts 9 of the next column with a reading being taken at each contact of the impedance of the respective cell. In the circuit 16, the values are stored from each cycle in a conventional memory and compared with the readings of the next and subsequent cycles to generate points on respective microorganism graph curves which can be outputted on a display 41. The plates 2 and 3 may be displaceable and the electrode plates 4 and 5 can be cleaned and autoclaved for reuse.

Figure 2:
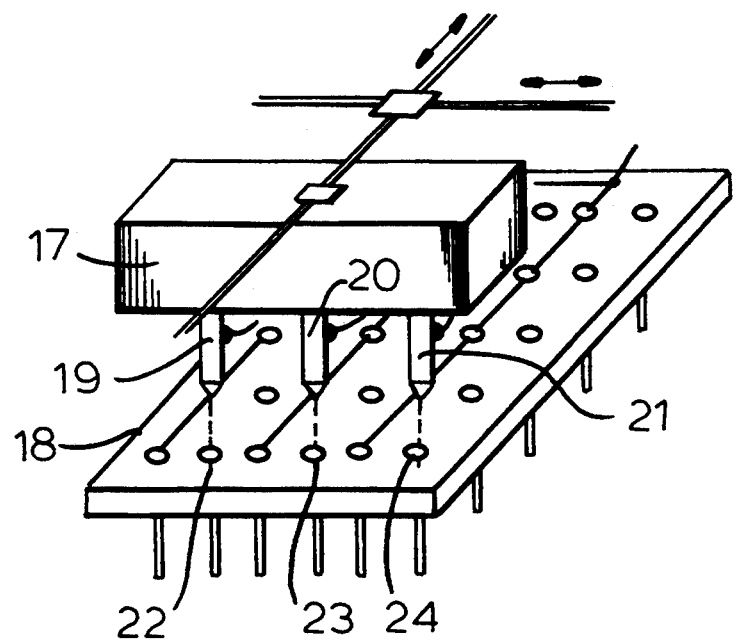
FIG. 2 is a perspective view illustrating an embodiment having a plurality of probes for engagement with contact pieces from a plurality of cells.

FIG. 2 shows that a measuring head can be provided with probes 19, 20 and 21 at the spacing of the contact pieces 9 along the row for simultaneous engagement with such contact pieces as is represented at 22, 23 and 24 upon displacement of the head 17 along a respective column.

Figure 3:
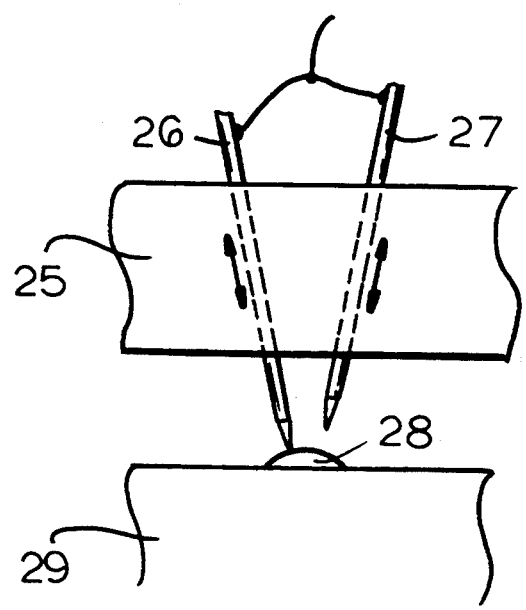
FIG. 3 is a fragmentary elevational view illustrating partial contacts for engagement with a contact piece in accordance with the principles described above.

As has been shown in highly diagrammatic form in FIG. 3, each probe 11, 19, 20, 21 can include a pair of partial contacts in the form of metal points 26 and 27 which can successively and jointly engage an electrode contact piece 28 so that respective contact resistances can be calculated and the dependency of the total impedance upon the contact resistances can be determined so as to yield impedance measurements Z free from the influence of the contact resistance.

We claim:

1. An apparatus for the fully automatic monitoring of microorganism multiplication, comprising:

a stationary support provided with a multiplicity of upwardly open cells containing respective samples of a microorganism culture, said cells being located in a cell array of rows and columns spaced along x and y axes of an x, y coordinate system;

at least one electrode assigned to each of said cells and adapted to contact the respective sample for an electrical measurement of an electrical impedance thereof;

a common electrode-carrier plate positioned above said support and said cells and carrying said electrodes, said electrodes being positioned in an electrode array corresponding to said cell array and with said electrodes extending downwardly into said cells;

respective contacts disposed upon an upper surface of said plate, electrically connected to each of said electrodes and disposed in a contact array corresponding to said cell and electrode array with contacts spaced along the x and y axes of said x, y coordinate system;

a sensing head above said plate and successively juxtaposable with said contacts and provided with a probe engageable with the contacts with which said head is juxtaposed and connected to an impedance measuring circuit; and a traveling carriage system movable along the x and y axes of said x, y coordinate system and defining paths parallel to rows of said contacts along said contact array and displacing said head along said paths.

2. The apparatus defined in claim 1 wherein said plate, said electrodes and said contacts form a unitary body raisable from and lowerable toward said cells and provided with said contact array.

3. The apparatus defined in claim 2, further comprising a sensor on said head responsive to a contact and connected to juxtapose said head with a detected contact with said probe in alignment therewith.

4. The apparatus defined in claim 3 wherein said head is formed with a plurality of probes for simultaneous engagement with a corresponding number of said contacts.

5. The apparatus defined in claim 4 wherein two electrodes are provided to engage the sample in each cell, one of the two electrodes being provided with the respective contact, the others of said two electrodes of all of said cells of said cell array being connected by a common ground conductor.

6. The apparatus defined in claim 2 wherein said head is formed with a plurality of probes for simultaneous engagement with a corresponding number of said contacts.

7. The apparatus defined in claim 2 wherein two electrodes are provided to engage the sample in each cell, one of the two electrodes being provided with the respective contact, the others of said two electrodes of all of said cells of said cell array being connected by a common ground conductor.

8. The apparatus defined in claim 1, further comprising a sensor on said head responsive to a contact and connected to juxtapose said head with a detected contact with said probe in alignment therewith.

9. The apparatus defined in claim 1 wherein said head is formed with a plurality of probes for simultaneous engagement with a corresponding number of said contacts.

10. The apparatus defined in claim 1 wherein two electrodes are provided to engage the sample in each cell, one of the two electrodes being provided with the respective contact, the others of said two electrodes of all of said cells of said cell array being connected by a common ground conductor.

* * * * *